(12) United States Patent
Plumptre

(10) Patent No.: US 11,052,200 B2
(45) Date of Patent: Jul. 6, 2021

(54) CAP FOR A DRUG DELIVERY DEVICE

(71) Applicant: Sanofi-Aventis Deutschland GMBH, Frankfurt am Main (DE)

(72) Inventor: David Aubrey Plumptre, Worcestershire (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 84 days.

(21) Appl. No.: 14/914,476

(22) PCT Filed: Aug. 26, 2014

(86) PCT No.: PCT/EP2014/068021
§ 371 (c)(1),
(2) Date: Feb. 25, 2016

(87) PCT Pub. No.: WO2015/028439
PCT Pub. Date: Mar. 5, 2015

(65) Prior Publication Data
US 2016/0199589 A1   Jul. 14, 2016

(30) Foreign Application Priority Data
Aug. 29, 2013   (EP) ..................................... 13182224

(51) Int. Cl.
*A61M 5/32*   (2006.01)
(52) U.S. Cl.
CPC ........ *A61M 5/3202* (2013.01); *A61M 5/3213* (2013.01); *A61M 2005/3201* (2013.01)

(58) Field of Classification Search
CPC ........ A61M 5/3202; A61M 2005/3201; A61M 5/3213; A61M 5/3204; A61M 5/3216
See application file for complete search history.

(56) References Cited

U.S. PATENT DOCUMENTS

| 533,575 A | 2/1895 | Wilkens |
| 2,495,080 A | 1/1950 | Storch |

(Continued)

FOREIGN PATENT DOCUMENTS

| CA | 2138528 | 2/1994 |
| CA | 2359375 | 7/2000 |

(Continued)

OTHER PUBLICATIONS

International Preliminary Report on Patentability in International Application No. PCT/EP2014/068021, dated Aug. 26, 2014, 8 pages.

(Continued)

*Primary Examiner* — Nathan R Price
*Assistant Examiner* — Dung T Ulsh
(74) *Attorney, Agent, or Firm* — Fish & Richardson P.C.

(57) ABSTRACT

A cap (120) for a drug delivery device (1) having a distal end (121) and a proximal end (122); the cap (120) having an opening at the proximal end and further comprising an outer cap element (130) and an inner cap element (131) being located inside the outer cap element (130), the inner cap element (131) comprising a deformable region (151) and a cap snap means (149); wherein the deformable region (151) of the inner cap element (131) is deformable into a gap (143) between the inner cap element (131) and the outer cap element (130).

16 Claims, 14 Drawing Sheets

(56) References Cited

U.S. PATENT DOCUMENTS

| | | | |
|---|---|---|---|
| 4,475,905 A * | 10/1984 | Himmelstrup | A61M 5/31551 604/208 |
| 4,865,591 A | 9/1989 | Sams | |
| 5,092,842 A | 3/1992 | Bechtold et al. | |
| 5,226,895 A | 7/1993 | Harris | |
| 5,226,896 A | 7/1993 | Harris | |
| 5,279,586 A | 1/1994 | Balkwill | |
| 5,304,152 A | 4/1994 | Sams | |
| 5,320,609 A | 6/1994 | Haber et al. | |
| 5,378,233 A | 1/1995 | Haber et al. | |
| 5,383,865 A | 1/1995 | Michel | |
| 5,391,157 A | 2/1995 | Harris et al. | |
| 5,480,387 A | 1/1996 | Gabriel et al. | |
| 5,492,248 A * | 2/1996 | Ortner | A45D 34/02 222/78 |
| 5,505,704 A | 4/1996 | Pawelka et al. | |
| 5,582,598 A | 12/1996 | Chanoch | |
| 5,626,566 A | 5/1997 | Petersen et al. | |
| 5,674,204 A | 10/1997 | Chanoch | |
| 5,688,251 A | 11/1997 | Chanoch | |
| 5,807,346 A | 9/1998 | Frezza | |
| 5,820,602 A | 10/1998 | Kovelman et al. | |
| 5,851,079 A | 12/1998 | Horstman et al. | |
| 5,921,966 A | 7/1999 | Bendek et al. | |
| 5,957,896 A | 9/1999 | Bendek et al. | |
| 5,961,495 A | 10/1999 | Walters et al. | |
| 6,004,297 A | 12/1999 | Steenfeldt-Jensen et al. | |
| 6,193,698 B1 | 2/2001 | Kirchhofer et al. | |
| 6,221,046 B1 | 4/2001 | Burroughs et al. | |
| 6,235,004 B1 | 5/2001 | Steenfeldt-Jensen et al. | |
| 6,248,095 B1 | 6/2001 | Giambattista et al. | |
| 6,277,099 B1 | 8/2001 | Strowe et al. | |
| 6,551,286 B1 | 4/2003 | Claessens | |
| 6,562,006 B1 | 5/2003 | Hjertman et al. | |
| 6,613,023 B2 | 9/2003 | Kirchhofer et al. | |
| 6,699,224 B2 | 3/2004 | Kirchhofer et al. | |
| 6,932,794 B2 | 8/2005 | Giambattista et al. | |
| 6,936,032 B1 | 8/2005 | Bush, Jr. et al. | |
| 7,169,132 B2 | 1/2007 | Bendek et al. | |
| 7,241,278 B2 | 7/2007 | Moller | |
| 7,678,084 B2 | 3/2010 | Judson et al. | |
| 8,187,233 B2 | 5/2012 | Harms et al. | |
| 2002/0052578 A1 | 5/2002 | Moller | |
| 2002/0062108 A1 * | 5/2002 | Courteix | A61M 5/3202 604/198 |
| 2002/0065483 A1 | 5/2002 | Leon et al. | |
| 2002/0120235 A1 | 8/2002 | Enggaard | |
| 2003/0050609 A1 | 3/2003 | Sams | |
| 2004/0052571 A1 | 3/2004 | Furukawa et al. | |
| 2004/0059299 A1 | 3/2004 | Moller | |
| 2004/0097883 A1 | 5/2004 | Roe | |
| 2004/0210199 A1 | 10/2004 | Atterbury et al. | |
| 2004/0267207 A1 | 12/2004 | Veasey et al. | |
| 2005/0113765 A1 | 5/2005 | Veasey et al. | |
| 2006/0079847 A1 * | 4/2006 | Crawford | A61M 25/0631 604/192 |
| 2006/0153693 A1 | 7/2006 | Fiechter et al. | |
| 2007/0016143 A1 | 1/2007 | Miller et al. | |
| 2007/0088261 A1 * | 4/2007 | Lew | A61M 5/3216 604/110 |
| 2009/0069753 A1 * | 3/2009 | Ruan | A61M 5/3202 604/192 |
| 2009/0275916 A1 | 11/2009 | Harms et al. | |
| 2012/0029442 A1 * | 2/2012 | Boyd | A61M 5/3202 604/197 |
| 2012/0041384 A1 * | 2/2012 | Finke | A61M 5/24 604/194 |
| 2012/0283696 A1 * | 11/2012 | Cronenberg | A61M 5/3213 604/506 |
| 2014/0025013 A1 * | 1/2014 | Dowds | A61M 5/3129 604/198 |
| 2014/0343503 A1 * | 11/2014 | Holmqvist | A61M 5/3202 604/192 |
| 2015/0174329 A1 * | 6/2015 | Takemoto | B65B 55/10 604/192 |
| 2015/0174337 A1 * | 6/2015 | Takemoto | A61M 5/3202 604/192 |
| 2015/0335830 A1 * | 11/2015 | Horita | A61M 5/3213 604/192 |
| 2016/0067413 A1 * | 3/2016 | Madin | A61M 5/3202 604/222 |
| 2016/0106929 A1 * | 4/2016 | Fournier | A61M 5/3202 604/192 |
| 2016/0144132 A1 * | 5/2016 | Scanlon | A61M 5/3202 604/192 |
| 2016/0193414 A1 * | 7/2016 | McLoughlin | A61M 5/24 604/192 |
| 2016/0271336 A1 * | 9/2016 | Thomsen | A61M 5/3137 |

FOREIGN PATENT DOCUMENTS

| | | |
|---|---|---|
| EP | 0295075 | 8/1988 |
| EP | 0496141 | 7/1992 |
| EP | 0498737 | 8/1992 |
| EP | 0897 729 | 2/1999 |
| EP | 0937471 | 8/1999 |
| EP | 0937476 | 8/1999 |
| EP | 1674289 | 6/2006 |
| EP | 1776975 | 4/2007 |
| GB | 0304822 | 3/2003 |
| GB | 2431732 | 2/2007 |
| GB | 0304823 | 11/2017 |
| JP | H0398094 | 10/1991 |
| JP | H09263087 | 10/1997 |
| WO | WO 93/07922 | 4/1993 |
| WO | WO 93/24160 | 12/1993 |
| WO | WO 1999/038554 | 8/1999 |
| WO | WO 2001/010484 | 2/2001 |
| WO | WO 02/030495 | 4/2002 |
| WO | WO 02/092153 | 11/2002 |
| WO | WO03/008023 | 1/2003 |
| WO | WO 03/080160 | 10/2003 |
| WO | WO 2006/084876 | 8/2006 |
| WO | WO2008/101829 | 8/2008 |
| WO | WO 2009/152397 | 12/2009 |
| WO | WO2015/028439 | 3/2015 |
| WO | WO2011/154490 | 12/2015 |

OTHER PUBLICATIONS

International Search Report and Written Opinion in International Application No. PCT/EP2014/068021, dated Aug. 26, 2014, 11 pages.

Rote Liste, "50. Hypophysen-, Hypothalamushormone, andere regulatorische Peptide u. ihre Hemmstoffe," Chapter 50, ed. 2008, 20 pages.

"Pen-injectors for medical use—Part 1: Pen-injectors—Requirements and test methods," International Standard, reference No. ISO 11608-1:2000(E), first edition Dec. 15, 2000, 32 pages.

* cited by examiner

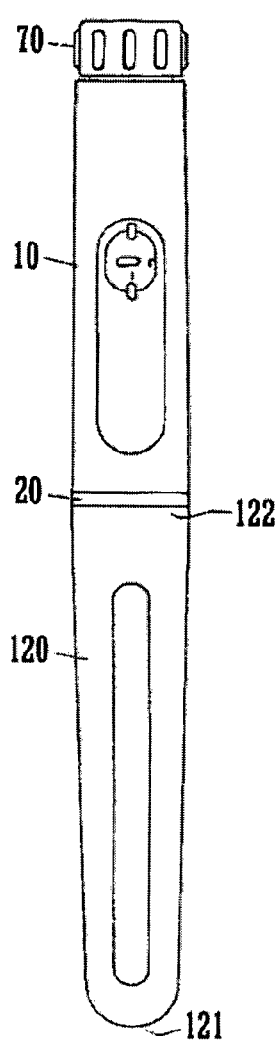
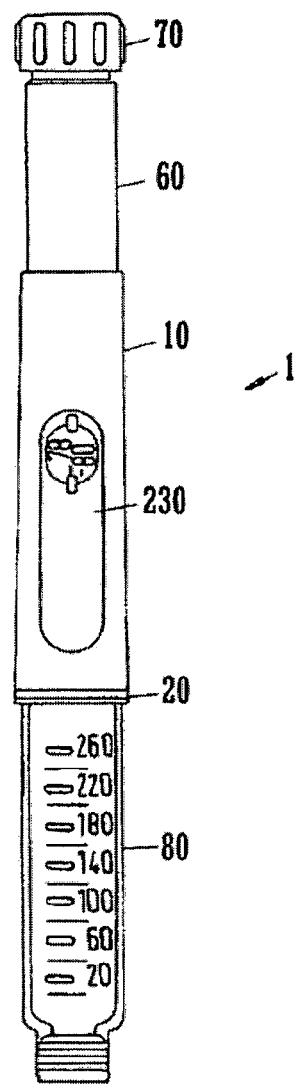

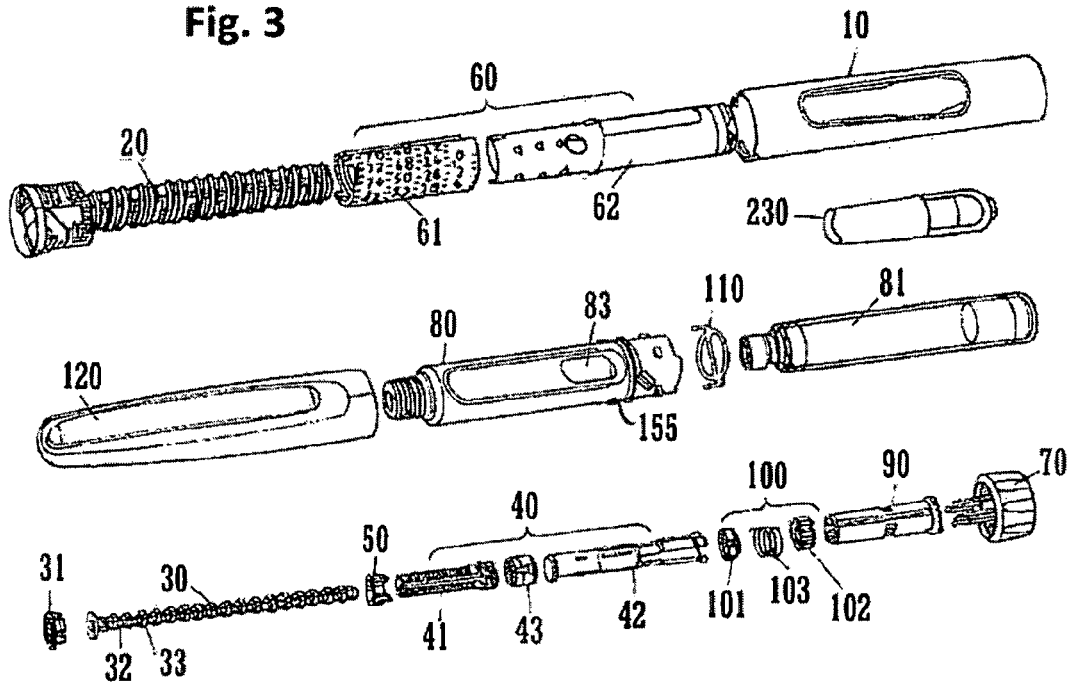
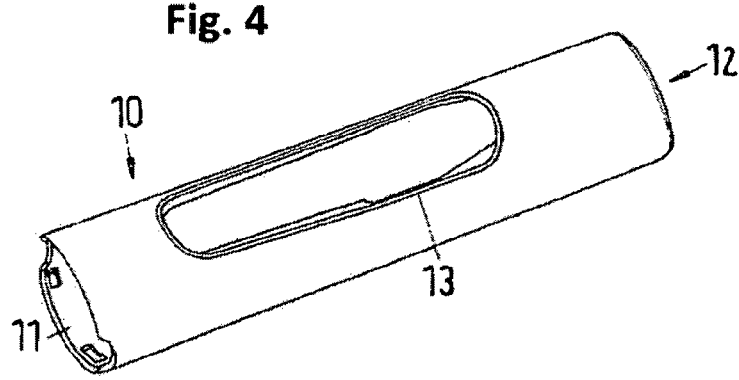

CAP FOR A DRUG DELIVERY DEVICE

CROSS-REFERENCE TO RELATED APPLICATIONS

This application is a U.S. national stage application under 35 USC § 371 of International Application No. PCT/EP2014/068021, filed on Aug. 26, 2014, which claims priority to European Patent Application No. 13182224.9, filed on Aug. 29, 2013, the entire contents of which are incorporated herein by reference.

The invention concerns a cap for a drug delivery device and a drug delivery device arrangement.

Pen type drug delivery devices apply where regular injection by persons without formal medical training occurs. This may be increasingly common among patients having diabetes where self-treatment enables such patients to conduct effective management of their disease. In practice, such a drug delivery device allows a user to individually select and dispense a number of user variable doses of a medicament. Alternatively fixed dose devices allow dispensing of a predefined dose without the possibility of increasing or decreasing the set dose.

There are basically two types of drug delivery devices: resettable devices (i.e. reusable) and non-resettable (i.e. disposable). For example, disposable pen delivery devices do not have removable pre-filled cartridges.

The distal part of a drug delivery device which may include the cartridge and/or a needle assembly may be protected by a cap. It is a desire, in particular with respect to non-disposable pen-type drug delivery devices, to provide an attachable cap for a drug delivery device that is robust and has a high-quality look and pleasant touch.

This aim is achieved by a cap for a drug delivery device according to claim 1, the cap having a distal end and a proximal end. The cap has an opening at the proximal end and further comprises an outer cap element. An inner cap element is located inside the outer cap element; the inner cap element comprises a deformable region and a cap snap means. The deformable region of the inner cap element is deformable into a gap between the inner cap element and the outer cap element.

The term "distal end" of the drug delivery device or a component thereof may refer to that end of the device or the component which is closest to the dispensing end of the device. The term "proximal end" of the drug delivery device or a component thereof may refer to that end of the device or the component which is furthest away from the dispensing end of the device.

The proximal end of a sleeve-shaped cap is the open end through which the distal part of the drug delivery device is inserted.

Such a cap allows cover and protection of the distal part of the drug delivery device. The cap may be releasably attached over the cartridge holder. The interaction of the cap snap means, the deformable region and the gap allows attaching the cap, safe attachment of the cap and detaching the cap. In one embodiment the cap may be sleeve-shaped, wherein the distal end is closed and the proximal end has an opening through which the distal part of the drug delivery device may be inserted into the cap. The cap is designed in such a manner that it covers a distal part of the drug delivery devices and is able to get into a snap connection with the drug delivery device. A snap connection is a form fitting connection between a snap means and a corresponding moveable or deformable snap means that may engage to the snap means. Protrusions may engage to cavities or noses/fingers may engage behind edges, for example.

The deformable region allows locking and releasing the snap connection with the drug delivery device. The deformable region may be made of an elastic material that returns to its original shape after being deformed. Deformation occurs when a force impacts on the deformable region. If the material is elastic, the region will return to its initial shape and size when the force is removed.

The cap snap means may engage with a cap retention means located on the drug delivery device, thereby forming the releasable snap connection. The cap snap means may comprise a raised portion, e.g. a finger or a nose. The raised portion locks into place behind an edge of the corresponding cap retention means located on the drug delivery device after attachment of the cap. Preferably the cap snap means is located on a proximal section of the cap, which may be a proximal section of the inner cap element.

The gap may be the space between the inner and outer cap elements spaced from another in the region of the deformable region. In one embodiment, the gap may be a cavity located on the inner surface of the outer cap element.

The combination of an inner cap element and an outer cap element allows providing optimised outer and inner components. The outer component may have a robust surface. The inner component may be made of a more sensitive material which may easily be produced and molded in the desired form.

The outer cap element may be made of metal, e.g. aluminium. In one embodiment gap is a cavity on the inside surface of the outer cap element; the cap may be formed as an at least partly circumferentially running recess on the inner surface of the outer cap element. This recess may be formed in an easy way, e.g. by deep drawing the proximal section of the outer cap element in such a manner that it is thinner than distal and middle sections and then folding back the proximal lip of the outer cap element. The thin region being distal with respect to the folded lip forms the cavity. The folded lip forms the proximal edge of the cavity. The thickness of the outer cap element in the region of the cavity is smaller than in the distal or middle sections of the outer cap element.

In one embodiment a deep drawn aluminium outer cap element has a rolled over edge to the open end. The application of this rolled end allows securing the inner cap component and allows additional space for the inner cap component to flex during attachment of the cap to the drug delivery device.

The cap snap means is located in the deformable region or adjacent to the deformable region; in the latter case it is preferably located proximally with respect to the deformable region. Deformation of the deformable region allows locking and releasing the cap snap connection with the drug delivery device.

In one embodiment the proximal end of the cap snap means is located proximally with respect to the proximal edge of the cavity of the outer cap element. This arrangement allows applying torque to the deformable region since the proximal end of the cap snap means remains in its position when forces impact to the cap snap means during attachment. Alternatively, the proximal end of the cap snap means is located distally with respect to the proximal edge of the cavity of the outer cap element.

The cap snap means may comprise a raised portion forming a nose or a finger that allows locking the cap in its position after attachment. The thickness of the inner cap element in at least a part of the deformable region is smaller than in other sections of the inner cap element. The deformable region can be formed such as the inner cap element has a cavity on the inner surface; the cavity being suitable for engaging to the raised cap retention means located on the drug delivery device.

Preferably the inner cap element is made of plastic which allow easy manufacturing.

In one embodiment the inner and outer cap elements are both sleeve-shaped; the inner cap element being suitable for receiving the distal section of the drug delivery device; the robust outer cap element serves for protection. The inner cap element and the outer cap element may be connected by suitable means; e.g. adhesive means, positive locking and/or friction locking.

In one embodiment the cap comprises a fixing element with a connection feature, the outer cap element having an opening, and the inner cap element comprising a corresponding connection feature. A section of the fixing element extends through the opening of the outer cap element such that the fixing element is connected to the inner cap element by an interaction of the connection feature and the corresponding connection feature. Such a fixing element may be a clip which allows connecting the drug delivery device by means of the cap to a shirt or jacket pocket.

A drug delivery device arrangement comprises a cap as described above and a drug delivery device comprising a cap retention means being suitable for forming a snap connection with the cap snap means.

The term "medicament" or "drug", as used herein, preferably means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyhepta¬decanoyl) human insulin.

Exendin-4 for example means Exendin-4(1-39), a peptide of the sequence H His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser- Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2, H-(Lys)6-des Pro36 [Met(O)14, Asp28] Exendin-4(1-39)-Lys6-NH2, des Met(O)14 Asp28 Pro36, Pro37, Pro38 Exendin-4(1-39)-NH2, H-(Lys)6-desPro36, Pro37, Pro38 [Met(O)14, Asp28] Exendin-4(1-39)-NH2, H-Asn-(Glu)5-des Pro36, Pro37, Pro38 [Met(O)14, Asp28] Exendin-4(1-39)-NH2, des Pro36, Pro37, Pro38 [Met(O)14, Asp28] Exendin-4(1-39)-(Lys)6-NH2, H-(Lys)6-des Pro36, Pro37, Pro38 [Met(O)14, Asp28] Exendin-4(1-39)-(Lys)6-NH2, H-Asn-(Glu)5 des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp(O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2)25, Asp28] Exendin-4(S1-39)-(Lys)6-NH2, H-Asn-(Glu)5-des Pro36, Pro37, Pro38 [Met(O)14, Trp(O2)25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

A non-limiting, exemplary embodiment of the invention will now be described with reference to the accompanying drawings, in which:

FIG. 1 shows a drug delivery device with a cap attached in accordance with the present invention;

FIG. 2 shows the drug delivery device of FIG. 1 with the cap removed and a dose of 79 units dialed;

FIG. 3 shows in an exploded view the components of the drug delivery device of FIG. 1;

FIG. 4 shows the outer body of the drug delivery device of FIG. 1;

FIG. 5b shows a detail of the inner body of FIG. 5a;

FIG. 7b shows a detail of the first display member of FIG. 7a;

Figure 5A:
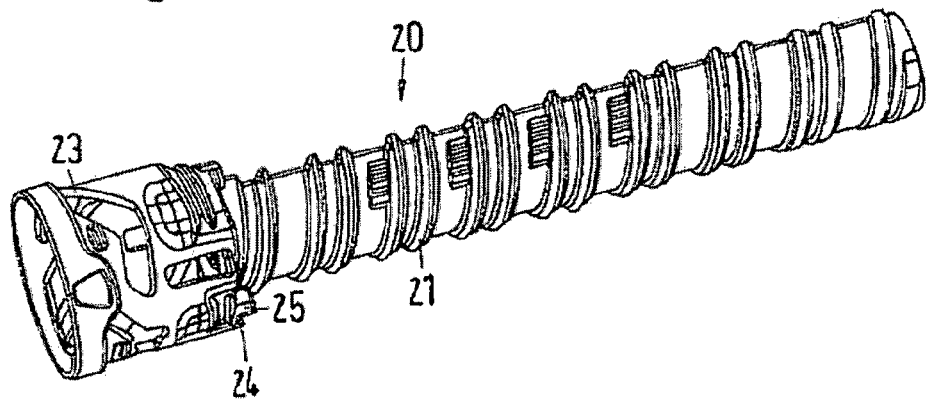
FIG. 5a shows the inner body of the drug delivery device of FIG. 1.

FIGS. 1 and 2 show a drug delivery device 1 in the form of an injection pen. The device has a distal end (lower end in FIG. 1) and a proximal end (upper end in FIG. 1). The component parts of the drug delivery device 1 are shown in FIG. 3 in more detail. The drug delivery device 1 comprises an outer housing part 10, an inner body 20, a piston rod 30, a driver 40, a nut 50, a display member 60, a button 70, a cartridge holder 80 for receiving a cartridge 81, a clutch 90, a clicker 100, a spring 110, a cap 120 and a window insert 230. A needle arrangement (not shown) comprising a needle hub and a needle cover may be provided as additional components, which can be exchanged as explained above. The piston rod 30 comprises a bearing 31. The driver comprises a distal driver part 41, a proximal driver part 42 and a coupler 43. The display member 60 comprises a number sleeve 61 and a dial sleeve 62. The clicker comprises a distal clicker part 101, a proximal clicker part 102 and a spring 103.

The outer housing part 10, which is shown in FIG. 4, is a generally tubular element having a distal part 11 for attaching the inner body 20 and a proximal part, which is provided with a rotational hard stop 12 on its inner surface (not shown) which contact mating faces of the display member 60 when the maximum units (in this example 80U) stop is engaged. The end face also serves as the end of dose dispense stop for the button 70, and the bore in the end face centers the display member 60 during both dialing and dispense. An aperture 13 is provided for receiving window insert 230. The outer body 10 provides the user with a surface to grip and react against during dispense.

Figure 17:
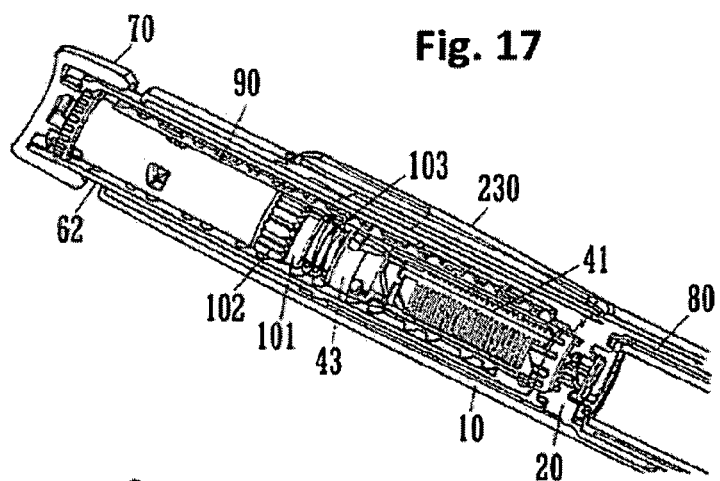
FIG. 17 shows a cut-away view of the proximal part of the drug delivery device of FIG. 1 in a zero unit position with the button released.
Figure 18:
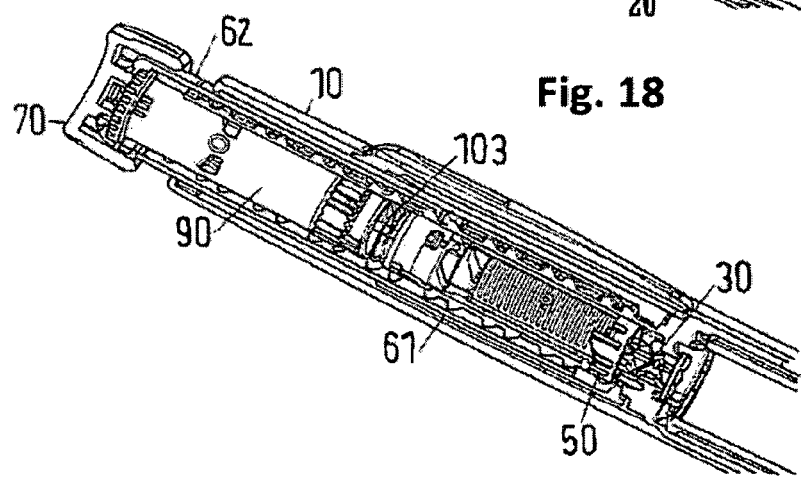
FIG. 18 shows a cut-away view of the proximal part of the drug delivery device of FIG. 1 in a position with some units dialed.
Figure 19:
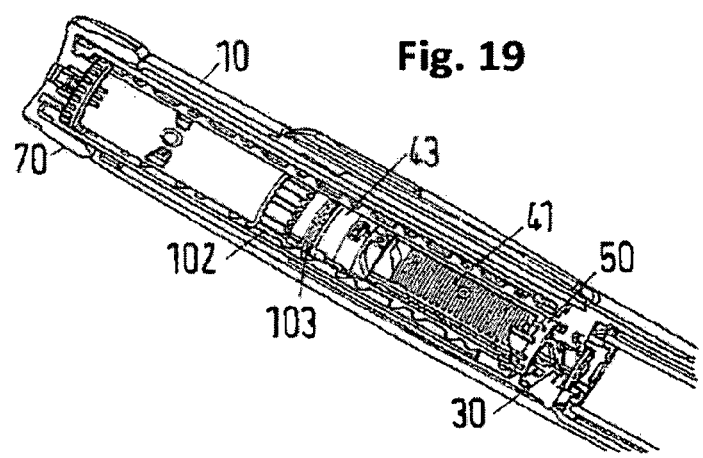
FIG. 19 shows a cut-away view of the proximal part of the drug delivery device of FIG. 1 in a zero unit position with the button pressed.

The inner body 20 is a generally tubular element having different diameter regions. As can be seen in FIGS. 17 to 19, the inner body 20 is received in the outer body 10 and permanently fixed therein to prevent any relative movement of the inner body 20 with respect to the outer body 10. The inner body has the functions to house the drive mechanism within, guiding the clickers and the last dose nut 50 via internal splines, to provide an internal thread through which the piston rod 30 (lead screw) is driven, to support and guide the number sleeve 61 and the dial sleeve 62 on an external thread form, to secure the cartridge holder 80 and to secure the outer body 10 and the window insert 230.

The outermost diameter of the inner body 20 also forms part of the visual design and remains visible when the cap 120 is secured to the cartridge holder 80 as a ring separating the cap 120 from the outer body 10. This visible ring also has depressions which align with the cap snap features on the cartridge holder 80 to indicate that the cartridge holder has been correctly fitted.

Figure 5B:
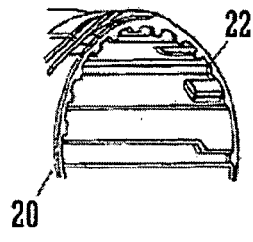

An external thread 21 is provided on the outer surface of the inner body 20. Further, splines 22 (FIG. 5b) are provided on the inner surface of the inner body 20. These internal splines 22 guide the clicker 100 axially during both dialing and dispense and also prevent the last dose nut 50 from rotating. Some of the splines may be wider to ensure correct rotational assembly of the internal components, and these wider splines may have a stepped entry and angled surface to encourage the last dose nut 50 to rotate up against the stop face on the distal drive sleeve 41 during assembly. At the open end shown in FIG. 5b there are an additional short splines which together with the alternating long splines 22 are used to rotationally lock the button 70 (dose dial grip) at the end of dispense and serve to increase the strength of the 0U dial stop when the button 70 is depressed. This is achieved by engagement with male spline features on the clutch component 90.

Bayonet features 23 guide the cartridge holder 80 into the mechanism during cartridge replacement, compressing the cartridge bias spring 110, and then back off the cartridge holder 80 a small distance in order to reduce axial play in the mechanism. Snap features inside the inner body 20 lock the cartridge holder 80 rotationally when it has been correctly fitted. The profile of these snaps aims to prevent the user from partially fitting the cartridge holder 80, the cartridge bias spring 110 ejecting the cartridge holder 80 if the snaps have not at least started to engage. A window retention nose 24 retains the window insert 230 when the outer body 10 and window insert 230 assembly is axially inserted onto the inner body 20. Two diametrically opposite stop faces 25 define the rotational end position for the number sleeve 61. This end position is the end of dose detent position for the minimum dose (0U).

The piston rod 30 is an elongate element having two external threads 32, 33 with opposite hand which overlap each other. One of these threads 32 engages the inner thread of the inner body 20. A disk-like bearing 31 is provided at the distal end of the piston rod 30. The bearing 31 may be a separate component as shown in FIG. 3 or may be attached to the piston rod 30 as a one-piece component via a predetermined breaking point.

The piston rod 30 transfers the dispense load from the driver 40 to the bearing 31, creating a mechanical advantage greater than 1:1 by converting the torque generated on the piston rod 30 by the driver 40 thread interface into additional axial load as the piston rod passes through the thread in the inner body 20. The piston rod 30 is reset by pressing on the bearing 31 and this in turn rotates the piston rod back into the inner body 20. This disengages and then rotates the distal drive sleeve 41, resetting the last dose nut 50 back to its starting position on the distal drive sleeve 41.

Figure 9:
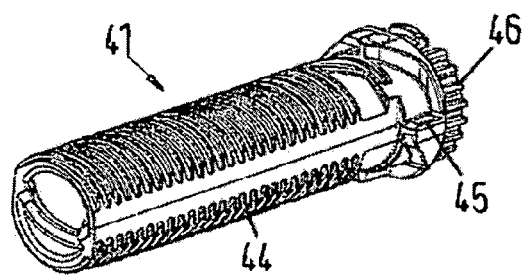
FIG. 9 shows a first driver component of the drug delivery device of FIG. 1.
Figure 10:
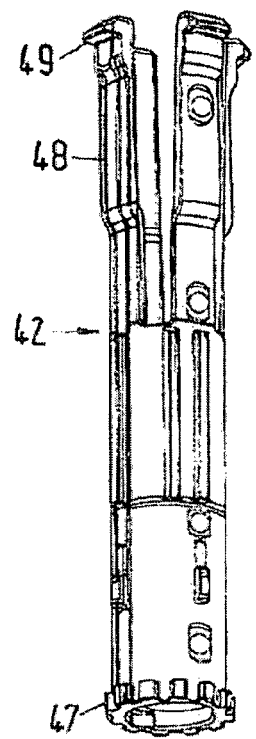
FIG. 10 shows a second driver component of the drug delivery device of FIG. 1.
Figure 11:
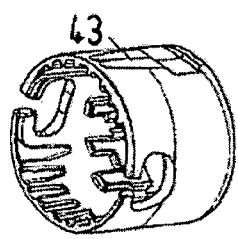
FIG. 11 shows a third driver component of the drug delivery device of FIG. 1.
Figure 12:
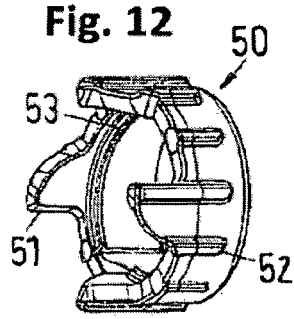
FIG. 12 shows the last dose nut of the drug delivery device of FIG. 1.
Figure 13:
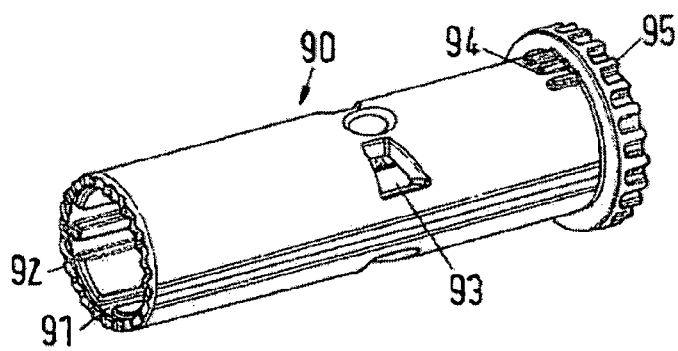
FIG. 13 shows a clutch component of the drug delivery device of FIG. 1.
Figure 14:
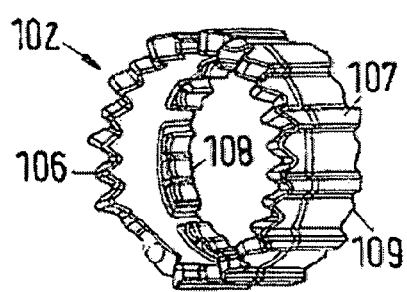
FIG. 14 shows a first clicker component of the drug delivery device of FIG. 1.
Figure 15:
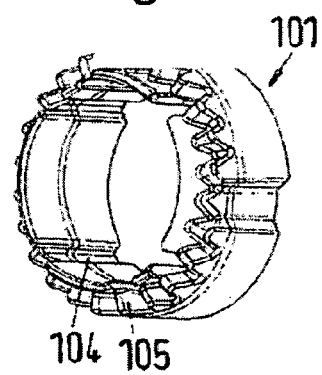
FIG. 15 shows a second clicker component of the drug delivery device of FIG. 1.

The driver 40 is a generally tubular element having in the embodiment shown in the Figures three components which are depicted in FIGS. 9 to 11 in more detail.

The distal drive sleeve 41 engages with the piston rod thread 33 to drive the piston rod 30 through the inner body 20 during dose delivery. The distal drive sleeve 41 is also permanently connected to the coupler 43 which in turn is releasably engaged through reset clutch features to the proximal drive sleeve 42. The two halves of the drive sleeve are rotationally and axially connected during dialing and dispense, but are de-coupled rotationally during device reset so that they can rotate relative to each other.

The external thread 44 engages with the last dose nut 50. The thread form has three stages, a shallow first stage (left hand side in FIG. 9) over which the nut 50 travels to count the majority of the units dialed, a fast stage over which the last dose nut moves rapidly axially prior to engaging the stop faces, and a final shallow section which ensures that when the stop faces have engaged, the axial restraint on the nut 50 extends over a reasonable length of thread form. Four equi-spaced stop faces 45 engage with mating stop faces 51 on the last dose nut 50 to limit the number of units that can be dialed. Splines 46 are provided at the proximal end of distal drive sleeve 41 to transfer torque from or to the coupler 43, which may be snapped on the distal drive sleeve 41.

The proximal drive sleeve 42 shown in FIG. 10 supports the clicker components 100 and the clutch 90 and transfers rotational movement from the dose button 90 to the coupler 42 and distal drive sleeve 41.

Teeth features 47 located at the distal end of proximal drive sleeve 42 engage with the reset clutch features on the coupler 43 to connect both halves of the drive sleeve during dialing and dispense. During reset these teeth 47 disengage.

Several splines are provided on the outer surface of proximal drive sleeve 42 engaging with distal proximal clicker part 10201, preventing relative rotation during dialing and dispense. Further splines, which are located in the middle region of proximal drive sleeve 42, engage with the clutch 90 component. They may be arranged to be non-rotationally symmetric so that the various clicker components cannot be assembled accidentally upside down.

The proximal portion of proximal drive sleeve 42 has four arms or fingers 48. A hook-like bearing surface 49 exists on the underside (as seen in FIG. 10) of flange segments on the end of the flexible fingers 48. The flexible fingers 48 are separated with gaps or slots that make space for the button 70 to snap to the clutch 90 and also enable these fingers to flex inwards during assembly of the proximal drive sleeve 42 to the dial sleeve 62. After assembly the hooks 49 retain the proximal drive sleeve 42 relative to the dial sleeve 62 under the reaction force from the spring 103. During dispense the button 70 depresses the spring 103 via the clutch 90 and the clicker components and this spring 103 is reacted through the coupler 43 to the proximal drive sleeve 42 which then through these bearing surfaces applies axial load to the dial sleeve 62. This axial load drives the dial sleeve 62 and hence number sleeve 61 along the helical thread of the inner body 20, back into the body of the device, until the 0U stop faces on the number sleeve 61 contact the inner body 20.

The coupler 43 shown in FIG. 11 rotationally couples the two halves of the drive sleeve together during dialing and dispense, whilst allowing them to de-couple during reset. The coupler 43 has to also transfer the last dose protection stop load from the proximal drive sleeve 42 to the distal drive sleeve 41. Two sets of teeth are provided in the coupler 43 for engaging teeth 46 and teeth 47, respectively. The coupler 43 is snapped onto distal drive sleeve 41 allowing limited relative axial movement with respect to the proximal drive sleeve 42.

The nut 50 is provided between the inner body 20 and the distal drive sleeve 41 of driver 40. Stop faces 51 are located on the proximal face of last dose nut 50 to limit the number of units that can be dialed if the stop faces 51 contact stops 45 of distal drive sleeve 41. The function of the last dose nut 50 is to prevent the user from dialing beyond a finite amount. This limit is based on the dispensable volume of the cartridge 81 and when reached, the user must replace the cartridge 81 and reset the device.

External ribs 52 of the nut 50 engage splines 22 of inner body 20. An internal thread 53 of the nut engages the external thread 44 of distal drive sleeve 41. As an alternative, splines and ribs could be provided on the interface between the nut 50 and the driver 40 and threads could be provided on the interface between the nut 50 and the inner body 20. As a further alternative, the nut 50 may be designed as e.g. a half nut.

The display member 60 is a generally tubular element which is composed of number sleeve 61 and dial sleeve 62 which are snapped together during assembly to axially and rotationally constrain these two components, which thus act as a single part.

Figure 8:
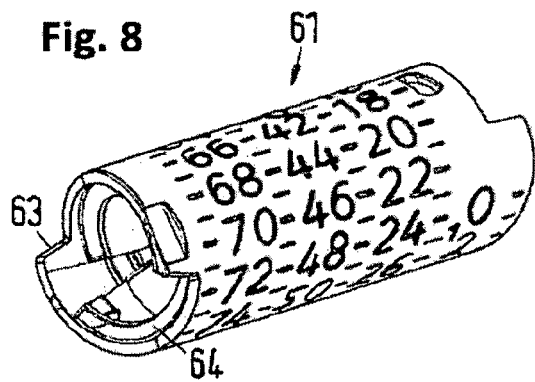
FIG. 8 shows a second display member component of the drug delivery device of FIG. 1.

The main functions of the number sleeve 61 depicted in FIG. 8 are to provide a surface onto which dose numbers can be printed to display the dialed dose, to guide the helical path of the internal mechanism during dialing to follow the helical thread form on the piston rod 30 when threaded to the inner body 20 and to attach to the dial sleeve 62.

The number sleeve 61 is designed to be fully enclosed in the outer body 10 during dialing and dispense and therefore only the dialed dose is visible to the user through the window aperture. The number sleeve has a 0U (minimum dose) stop face 63 to limit its travel when dialed in but the 80U (maximum dose) stop faces that limit the dialed out condition are located on the dial sleeve 62. At the end of each dispense stroke, this stop face 63 engages with mating surface 25 on the inner body 20 to limit the rotational position of the number sleeve 61.

A helical drive face 64 forms a thread that guides the number sleeve 61 during dialing and dispense to follow the helical path 21 on the inner body.

The dial sleeve 62 is assembled to the number sleeve 61 such that once assembled, no relative movement is allowed. The parts are made as separate components to enable both molding and assembly. Also, whereas the number sleeve 61 is preferably white to give contrast for the e.g. black dose numbers, the dial sleeve 62 color can be chosen to suit the aesthetics or perhaps to distinguish the drug type.

At the dose proximal end, the dial sleeve 62 has internal clutch features 65 that engage with the clutch component 90 during dialing and disengage from the clutch during dispense. These clutch features 65 rotationally lock the dial sleeve 62 to the clutch 90 during dialing and when the 0U and 80U stops are engaged. When the button 70 is depressed these clutch features disengage to allow the clutch 90 and drive mechanism to move axially whilst the dial sleeve 62 and number sleeve 61 spin back to the 0U start position.

The dial sleeve 62 rotates out during dialing through its engagement with the clutch 90 and number sleeve 61, and rotates back in during dispense under the axial force applied by the proximal drive sleeve 42 to a flange-like bearing face 66 on the end of the dial sleeve. This bearing face 66 engages with the flexible arms 48 of the proximal drive sleeve 42 during dispense. Two diametrically opposite faces 67 engage with the outer body 10 when the maximum dose (e.g. 80U) has been dialed, forming the maximum dose stop faces.

A ratchet arm 68 engages with ratchet features on the button 70 (dose dial grip) to provide audible feedback during dispense, giving one click per unit delivered. Further, this prevents the user from gripping and rotating the number sleeve 61 outwards from a partially dialed out position whilst holding the button 70 pressed in. This would back wind the piston rod 30 which would result in an under dose on the subsequent dialed dose. It may further strengthen the 0U stop.

Figure 16:
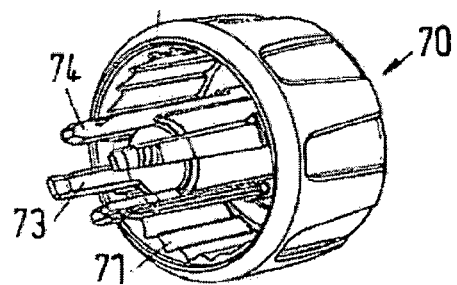
FIG. 16 shows the button of the drug delivery device of FIG. 1.

The button 70 which is shown in FIG. 16 serves as a dose dial grip and is retained by the clutch 90 to transfer the actions of the user to the clutch. It also carries ratchet teeth 71 that engage the ratchet arm 68 on the dial sleeve 62, which serves as the dispensing clicker giving audible feedback (ratchet clicks), and an end face 72 which serves as the dose completion stop face with the outer body 10. This end face 72 thus serves to define the end position during dispense when it contacts the outer body 10 to provide a very positive stop improving dose accuracy.

A central sleeve-like portion of button 70 is provided with four arms 73 having hook-like snap features 74 at their respective distal ends. The arms 73 form splined surfaces engaging with the clutch 90 to transfer torque from the button 70 through the clutch to the dial sleeve 62 and proximal drive sleeve 42. The snap features 74 engage apertures in the clutch 90 and are designed with angled undercut faces to maintain engagement when an axial load is applied to pull the button 70 out of the pen body 10. The space between arms 73 defines pockets giving clearance for the flexible arms 48 of proximal drive sleeve 42 to slide freely relative to the button 70 and clutch 90 when the button 70 is depressed and released during dose dispense.

Figure 6:
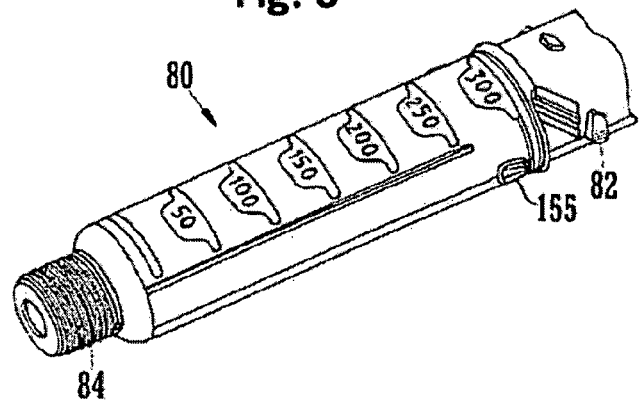
FIG. 6 shows the cartridge holder of the drug delivery device of FIG. 1.
Figure 7A:
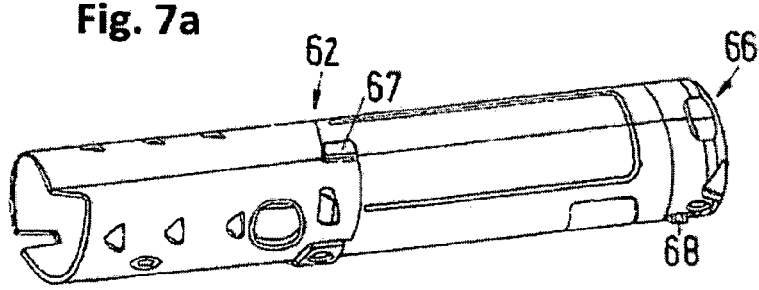
FIG. 7a shows a first display member component of the drug delivery device of FIG. 1.
Figure 7B:
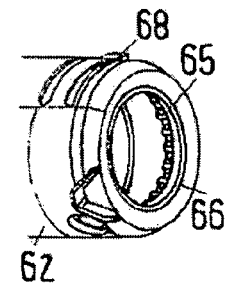

The cartridge holder 80 attaches to the inner body 20 with a bayonet connection 82 and houses the glass ampoule or cartridge 81 containing the medication to be dispensed. The cartridge holder 80 includes an aperture 83 in the rear face (as seen in FIG. 6) which if gripped by the user prevents the ampoule from falling out when the cartridge holder is removed from the inner body 20. The front face is printed with a dose number scale. The threaded distal end 84 is used to attach disposable pen needles.

A tubular clutch 90 is provided between the display member 60 and the button 70. The clutch is fixed relative to and retains the button 70 and together they travel axially relative to the proximal drive sleeve 42 when the button 70 is depressed during dispense, disengaging the clutch teeth from the dial sleeve 62. It also transfers torque from the button to the proximal drive sleeve 42, and the dialing and 0U/80U stop loads from the button via the clutch teeth to the dial sleeve and number sleeve.

Drive sleeve splines 91 provided on an inner surface of the clutch engage with the proximal drive sleeve 42. At the distal end face, clutch biasing teeth 92 are provided which mate with similar teeth on the proximal clicker part 102 to ensure that in the button out position (dialed dose) the clutch is locked in rotation to the proximal clicker part 102 under the biasing action of the clutch spring 103. The teeth 92 are shallow in height to prevent the proximal clicker part 102 from engaging with splines on the proximal drive sleeve 42 during dialing. Four snap apertures 93 serve to retain the snap features 74 of button 70. Near its proximal end, the clutch has splines 94 which at the end of dispense with the button 70 depressed lock to the inner body 20 to prevent the user from rotating the button 70 below the 0U position.

Clutch teeth 95 engage with clutch teeth 65 of the dial sleeve to rotationally couple the button 70 via the clutch to the number sleeve 61. During dispense the clutch is moved axially so as to disengage these clutch teeth 95 releasing the dial sleeve 62 to rotate back into the device whilst the clutch 90 and hence driver 40 move axially to dispense the dose.

The clicker 100 comprises a distal clicker part 101, a proximal clicker part 102 and a spring 103. The clutch spring 103 serves to bias the button 70 out so that at the end of a dose the button 70 pops out, re-engaging the clutch 90 with the dial sleeve 62 ready for dialing. Further, it provides the spring force for the clicker components to act as clickers and also as detent positions for the number sleeve 61. In addition, it holds the two halves of the drive sleeves 41, 42 in rotational engagement during dialing and dispense, whilst allowing them to disengage during device reset.

The distal clicker part 101 is permanently splined to the proximal drive sleeve 42 and engages with the proximal clicker part 102 which in turn is splined to the inner body 20. During dialing when the drive sleeve is rotated relative to the inner body, the two clickers 101, 102, rotate relative to each other under the compression force of the clutch spring 103. This force combined with the clicker teeth formed on the end face of each clicker provides the clicks and also the detent dialing positions.

During dispense the two clickers 101, 102 are pressed together under the dispense load and therefore prevent relative rotation between the proximal drive sleeve 42 and inner body 20, driving the piston rod forwards to deliver the dose. The splines 104 on the inner bore rotationally couple the distal clicker part 101 to the proximal drive sleeve 42 at all times, but allow free axial movement when the button 70 is depressed during dispense and when the two clickers ride over each other during dialing. The profile of the clicker teeth 105, 106 on both distal clicker part 101 and proximal clicker part 102 are identical and ride over each other under the compressive load from the spring 103 during dialing.

The proximal clicker part 102 is permanently splined to the inner body 20 by external splines 107 which prevent relative rotation with the inner body during both dialing and dispense, providing clicks during dialing and locking the proximal drive sleeve 42 in rotation during dispense. Additional cylindrically shaped splines 108 also couple the proximal clicker part 102 rotationally to the proximal drive sleeve 42 when the button 70 is depressed, this preventing the user from dialing past 80 units with the button depressed. Proximal clicker part 102, in addition to the primary clicker teeth 106, has clutch biasing teeth 109 on the opposite end face. These teeth mate with similar teeth 92 on the clutch to ensure that in the button out position (dialed dose) the clutch is locked in rotation to the proximal clicker part 102 under the biasing action of clutch spring 103.

The cartridge bias spring 110 is assembled as two components one after the other, the lower first and the upper second. The spring combination serves to apply an end load to the cartridge 81 at extremes of tolerance so as to bias it forwards onto the end face of the ferrule in the cartridge holder 80. This ensures that when the user removes and attaches a needle, the friction between the needle cannula and septum of the cartridge does not move the cartridge 81 axially relative to the cartridge holder 80. The bias spring 110 also acts to provide a force against which the user has to connect the cartridge holder 80 and this may add to the tactile feedback of this bayonet joint. The spring 100 also serves to eject the cartridge holder 80 if the cartridge holder is not rotated into a secure position, highlighting this error to the user.

The cap 120 serves to protect the cartridge holder 80 from damage and the cartridge 81 itself from dust dirt ingress on to the area around the septum. The cap is designed to accommodate a standard pen injector needle.

The window insert 230 may include a lens to magnify the dose numbers e.g. by approximately 25% from their printed size. The window insert 230 may be back printed to protect the printed surface from abrasion and also to maximize the light entering through the window aperture, giving uniform illumination of the dose numbers and white area around these numbers. Arrows may be printed adjacent to the window aperture that indicate the dose dialed.

In the following, the function of the drug delivery device and its components will be explained in more detail with reference to FIGS. 17 to 19.

To use the device, a user has to select a dose. In the start (at rest) condition as shown in FIG. 17 the display member 60 indicates the number of doses dialed to the user. The number of dialed units can be viewed through the dose window 230 in the outer body 10. Due to the threaded engagement between the display member 60 and the inner body 20 rotation of the button 70 in a clockwise fashion causes the display member 60 to wind out of the device and incrementally count the number of units to be delivered. FIG. 18 shows an intermediate stage of dialing (e.g. 7 of 80 units).

During dose setting button 70, driver 40 and display member 60 are rotationally locked together via clutch 90. Further, button 70, driver 40 and display member 60 are axially coupled. Thus, these three components wind out of the outer housing 10 during dose setting. Clockwise rotation of the button 70 causes the driver 40 to rotate and in doing so it advances along the piston rod 30 which remains fixed throughout dialing. The clicker arrangement 100 provides tactile and audible feedback to the user when dialing doses. At the maximum settable dose of 80 units, the stop features 12 and 67 engage to prevent further dialing.

The last dose nut 50 provides the function of counting the number of dispensed units. The nut 50 locks the device at the end of cartridge life and as such no more drug can be dialed by the user. The last dose nut 50 and the driver 40 are connected via a threaded interface as explained above. Further, the last dose nut 50 is assembled into splines 22 such that the nut 50 and the inner body 20 are rotationally locked together (at all times). Rotation of the driver 40 during dialing causes the nut 50 to advance along the thread 44. The nut 50 is free to slide axially within the inner body 20 at all times which allows advancement of the nut. The change in pitch of thread 44 shown in FIG. 9 towards the final doses axially accelerates the advancement of the nut 50 towards the end of cartridge life lockout condition. At the end of life condition, the stop features 51 of the last dose nut 50 contact the corresponding features 45 on the driver 40. The splined contact with inner body 20 reacts any torque transmitted by these stop features 45.

With the desired dose dialed, the device 1 is ready for dose dispensing. This basically requires pushing button 70 which will result in a disengagement of the clutch 90 from dial sleeve 62 thus allowing relative rotation between the display member 60 and the button 70. In all conditions the driver 40 and the button 70 are rotationally locked together by engagement of arms 73 and fingers 48 and by splines 91 engaging corresponding splines on proximal drive sleeve 42. Thus, with the clutch 90 disengaged (button 70 pushed in) button 70 and driver 40 are rotationally locked together with the button 70, the driver 40 and the display member 60 still being axially coupled.

When dispensing a dose, the dose button 70 and clutch 90 are moved axially relative to the mechanism compressing the clutch spring 103. Because the proximal clicker part 102 is splined to the inner body 20 and the axial load passing through the clicker teeth 105, 106 locks the distal clicker part 101 in rotation to the proximal clicker part 102, the mechanism is forced to move axially whilst the dial sleeve 62 and number sleeve 61 are free to spin back into the outer housing 10. The interaction of mating threads between the piston rod 30, driver 40 and inner body 20 delivers a mechanical advantage of 2:1. In other words, axially advancing driver 40 causes the piston rod 30 to rotate which due to the threaded engagement of piston rod 30 with the inner body 20 advances the piston rod. During dose dispensing dispense clicker 68, 71 is active which involves button 70 and display member 60. The dispense clicker provides primarily audible feedback to the user that drug is being dispensed.

The end of this step is shown in FIG. 19. At this point the dose is complete and when the user removes the force from the end of the dose button 70, the clutch spring 103 pushes this dose button 70 rearwards, re-engaging the teeth 65 and 95 between the clutch and the dial sleeve.

Resetting the device starts with removal of the cartridge holder 80 and replacing an empty cartridge with a full cartridge 81. As the cartridge holder is re-attached, the bung of the new cartridge contacts bearing 31, thus pushing piston rod 30 back into the housing. Initially, the piston rod 30 screws into the inner body 20, thereby axially disengaging the coupler 43 from the proximal drive sleeve 42 against the biasing force of spring 103. Once disengaged the coupler 43 is free to start rotating together with distal drive sleeve 41 and continues to do so as the cartridge holder 80 is moved axially into engagement with the inner body 20. Thus, the distal drive sleeve 41 rotates with respect to the proximal drive sleeve 42 which is still rotationally constrained in inner body 20 as clicker parts 101 and 102 are pressed together by compressed spring 103. As the distal drive sleeve 41 rotates, last dose nut 50 is reset to its (distal) start position. Coupling the cartridge holder 80 to inner body 20 backs off the mechanism due to the bayonet structure 23 allowing re-engagement of the proximal drive sleeve 42 with coupler 43 and thus the distal drive sleeve 41.

In the following the cap 120 is described in more detail with reference to FIGS. 20 to 30. FIGS. 20 to 25 illustrate the attachment means of the cap 120.

The cap 120 having a distal end 121 and a proximal end 122 serves to cover and protect the cartridge holder 80 from damage and the cartridge 81 itself from dust and dirt ingress on to the area around the septum. The cap 120 is designed to accommodate a distal part of the pen injector which is moved into the cap 120 through a proximal opening of the cap 120. The cap 120 may be attached to the drug delivery device 1 is such a manner that the needle arrangement 180 attached to the cartridge and the cartridge holder 80 are located inside the cap 120. The cap 120 is detached before use of the drug delivery device 1. The inside of the cap 120 is formed such that there is enough space for the needle arrangement 180 attached to the cartridge and the cartridge holder 80. Means (not shown in FIGS. 20 to 25) for guiding and holding the cartridge holder 80 and the needle arrangement 180 may be provided on the inner surface of the cap 120.

Figure 20:
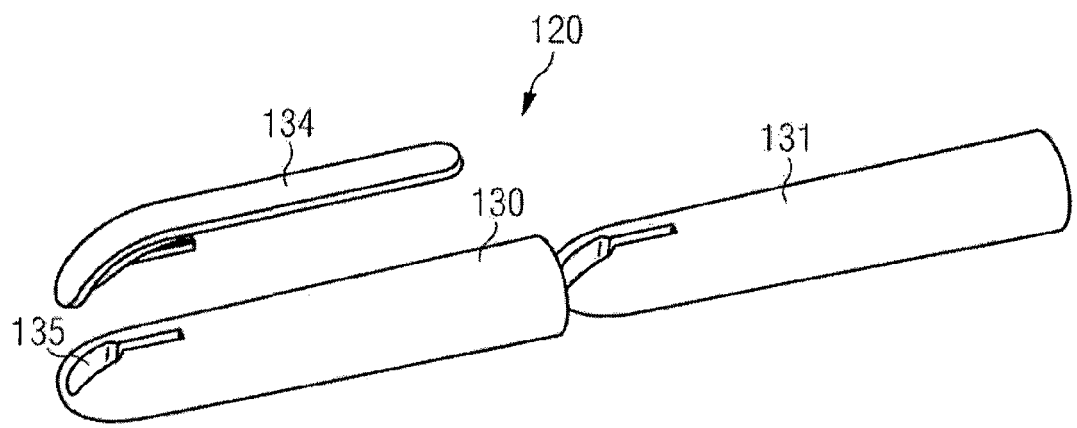
FIG. 20 shows an exploded view of a cap.

FIG. 20 shows an exploded view of the cap 120 comprising an outer cap element 130, an inner cap element 131 and a clip element 134. The outer and inner cap elements 130, 131 are made by a metal sleeve and a plastic sleeve, respectively, that can be assembled together to form the removeable cap 120. The outer and inner cap elements 130, 131 are connected by suitable means, e.g. adhesive means, positive locking and/or friction locking. The clip element 134 allows connecting the injector pen 1 by means of the cap 120 to a shirt or jacket pocket and is always handy for that reason. An aperture 135 in the outer cap element 130 enables the clip element 134 to snap to the inner cap element 131.

The outer cap element 130 is preferably made of metal; the inner cap element 131 is preferably made of plastic. The combination of the metal outer cap element 130 and the plastic inner cap element 131 allows providing a high-quality look and pleasant touch. The cap 120 is not too heavy and allows comfortable handling. The design of the inner component of the cap 120 allows retaining the clip element 134 and provides sufficient space to accommodate a standard needle and needle cover fitted to cartridge holder 80 inside the cap 120.

The outer cap element 130 may be a 0.4 mm to 0.6 mm thick aluminium element that provides a metal skin over the polymer inner cap element 131. The form of the cap 120 may be similar to one of a cap completely made of plastic. Such a cap 120 may substitute a cap completely made of plastic with no change in the tactile feel during attachment. Similar plastic features will not increase the risk of wear that may otherwise occur if attaching a plain metal sleeve to the existing plastic cartridge holder retention features.

The inner and outer cap elements 131, 130 are sleeve-shaped. The metal sleeve can be drawn from a metal sheet and then anodised over at least the outer surface. The anodising provides a high quality and hard wearing exterior surface to the cap 120 and enables the cap 120 to be given a variety of metallic colours. The removable cap 120 comprising the metal outer cap element 130 and the plastic inner cap element 131 can then be attached to a pen housing/mechanism which may be also made with a similar metal sleeve, to provide a reusable injection device that has a high quality aesthetic and robust surface.

This design minimises cost and provides robust hard wearing features. Hence the use of a combination of metal and plastic sleeve-shaped components enables the plastic sleeve to be moulded with features that attach to the plastic cartridge holder cap retention means.

Figure 21:
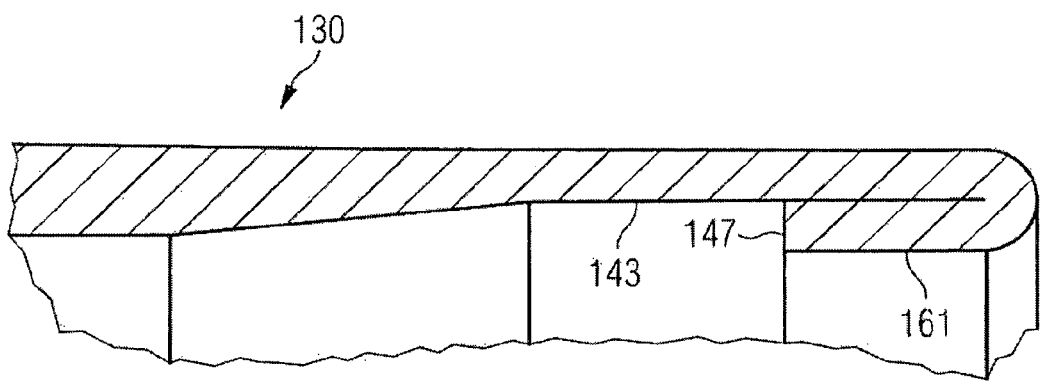
FIG. 21 shows a sectional view of a proximal region of an outer cap element.
Figure 22:
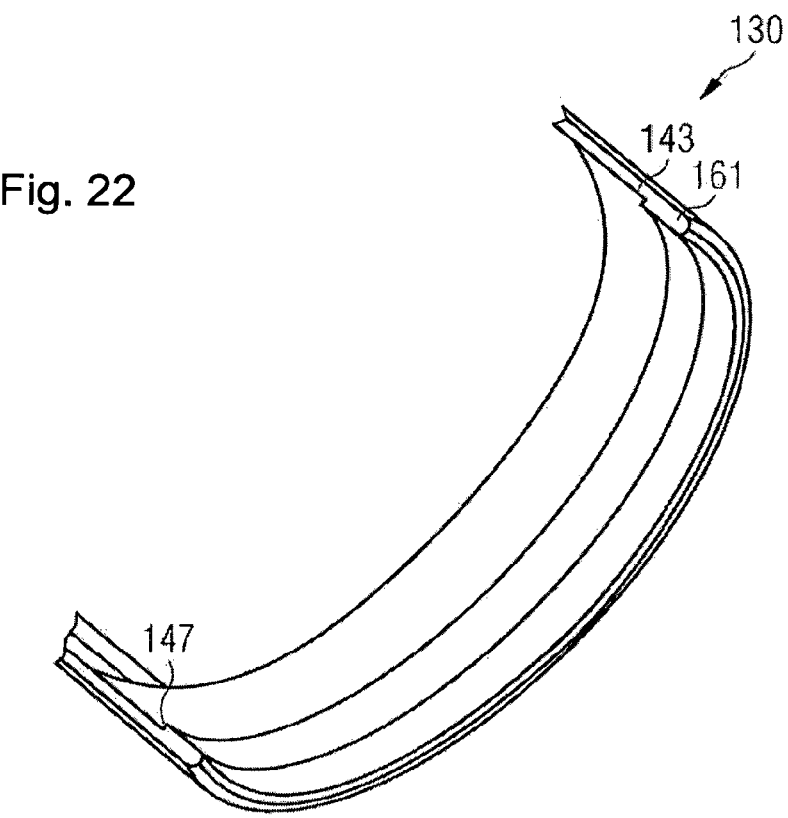
FIG. 22 shows a three-dimensional cut out view of the outer cap element.

FIG. 21 shows a sectional view of a proximal region of the outer cap element 130. FIG. 22 shows a three-dimensional cut-out view this component. The outer cap element 130 is formed by a metal sleeve deep drawn with reduced thickness at the open end section. The very proximal region is rolled over to form a rounded or folded end 161. Such rolling back of the material may form a beading. In this embodiment the material of the outer cap element 130 has been bent once. Nevertheless, the material may be bent more than once. Such bending allows forming a sharp edge 147 on the inner surface of the outer cap element 130.

Due to the thinner material of the open end, which is caused by the deep drawn process, and then forming the beading, a circumferential recess 143 is formed on the inner surface of the outer cap element 130. This recess 143 serves as space into which the inner cap element 131 can deform when attaching the cap 120 to the cartridge holder 80. The sharp edge 147 is the proximal edge of the recess 143, the edge 147 serving to retain the plastic inner cap element 131 after assembly.

Figure 23:
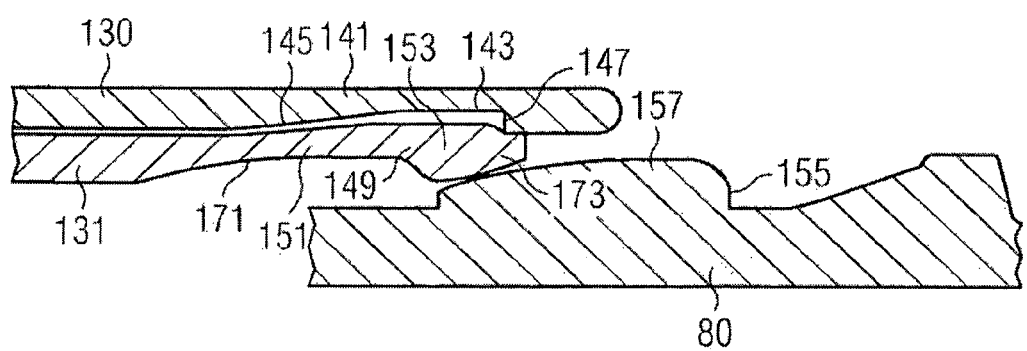
FIG. 23 shows a sectional view of the proximal section of the cap during attachment.

FIG. 23 shows a sectional view of a proximal section 141 of the cap 130 during attachment to the drug delivery device 1. During attachment the cap 120 including the inner and outer cap elements 131, 130 moves proximally with respect to the cartridge holder 80 in such a manner that the cartridge holder 80 moves into the cap 120.

The outer cap element 130 has a proximal section 141 comprising a cavity 143 on the inner surface of the outer cap element 130. The cavity 143 is formed as a circumferentially running recess in this embodiment. Alternatively the cavity 143 may have another form which may correspond with the form and size of the deformable region 151 of the inner cap element 131.

The thickness of the outer cap element 130 in the region of the cavity 143 is smaller than the thickness of a distal section or a middle section of the outer cap element 130. The distal edge 145 of the cavity 143 is formed ramp-shape which allows a gentle transition between the middle section of the outer cap element 130 and the cavity 143 located in the proximal section 141. The proximal edge 147 of the cavity 143 is steeper than the distal edge 145 and formed as a sharp edge.

The inner cap element 131 comprises cap snap means 149 located on the inside of a proximal section of the inner cap element 131 and suitable for engaging with a cap retention means 155 located on the cartridge holder 80 of the drug delivery device 1. The cap snap means 149 is formed by at least a proximal part of the deformable region 151 that may be deformed during attachment and detachment in order to lock the cap snap means 149 to the cap retention means 155 of the drug delivery device 1 and to release the cap snap means 149 from the cap retention means 155. The cap snap feature 149 comprises a raised nose 153 or finger and a cavity 171 where the inner cap element 131 in the region of the cavity 171 is thinner than in other regions; the cavity 171 may be formed by the deformable region 151. The nose 153 has a proximal slope being less steep than a distal slope.

The reduced thickness of the inner cap element's cavity 171 enables the deformation of the cap snap means 149, thereby allowing engaging to the cap retention feature 155. Due to the cavity 143 of the outer cap element 130 there is a gap between the outer and inner cap elements 130, 131. The deformable region 151 is deformable into the cavity 143 of the outer cap element 130. In other words, the deformable region 151 is deformable into the gap between the outer and inner cap elements 130, 131.

The proximal end 173 of the cap snap means 149 extends proximally over the proximal edge 147 of the cavity 143; the proximal edge 147 preventing outwards movement of the proximal end 173 of the cap snap means 149 and to hold this end circular.

The cap retention means 155 is located on the outer surface of the plastic cartridge holder 80. The cap retention means 155 comprises an elevation 157 which may have a base area formed as trapezium, circle, triangle or any other shape. In one embodiment two elevations 157 may be arranged on opposite sites of the cartridge holder 80, as shown in FIGS. 3 and 6. In one embodiment there are two or more than two elevations that are arranged equally or non-equally spaced on the drug delivery device 1.

The elevation 157 has proximal and distal slopes; the latter being less steep than the proximal slope of the elevation 157. The distal slope enables easy sliding of the proximal slope of the nose 153 over the top of the elevation 157 during attachment. The steeper slopes of both the elevation 157 and the nose 153 hinder distal movement of the nose 153 once it has moved over the top of the elevation 157, thereby preventing backward movement of the nose 153 after attachment. However, the impact of a sufficient force by the user pulling the cap 120 distally pulls the nose 153 over the elevation 157 again, thereby allowing detaching the cap 120. Since the distal slope of the nose 153 and the proximal slope of the elevation 157 are steeper, the force required for detachment is higher than for attachment, which prevents accidental detachment of the cap 120. Nevertheless, alternative nose 153 and elevation 157 embodiments may have other slope designs, which may be symmetrical.

When the nose 153 slides over the elevation 157, the nose 153 is pushed towards the outer cap element 130. Since the proximal end 173 of the cap snap means 149 is held in its position by the proximal edge 147 of the outer cap element 130, the resulting torque deforms the deformable region 151 outwardly and allows the nose tip sliding over the elevation 157. The cavity 143 of the outer cap element 130 allows space to accommodate at least some of the deformation of the plastic inner cap element 131 when the nose 153 slides over the elevation 157 during attachment of the cap 120.

Figure 24:
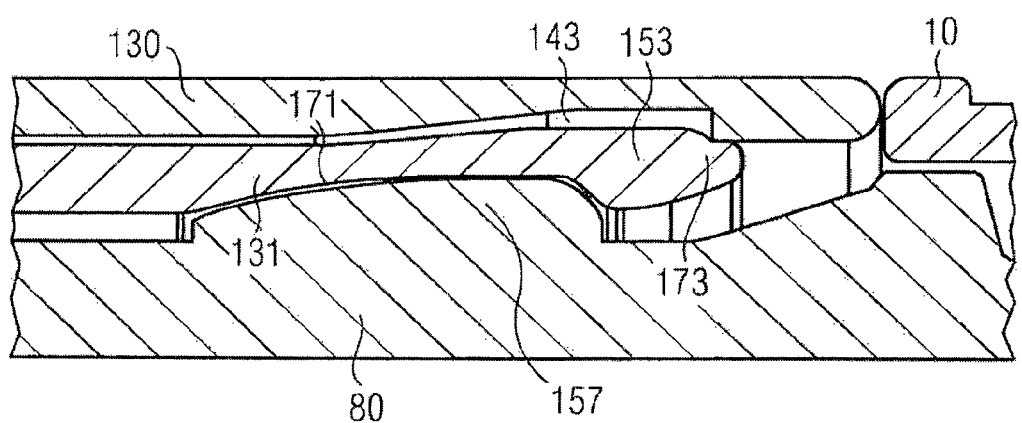
FIG. 24 shows a sectional view of the proximal section of the cap after attachment.

FIG. 24 shows a sectional view of the proximal section of the cap 120 after attachment to the drug delivery device 1.

The nose 153 is engaged behind the proximal edge of the elevation 157. The elevation 157 engages to the cavity 171 of the inner cap element 131. Though the nose 153 has slid over the elevation 157, the cap snap feature 149 is still deformed into the cavity 143 of the outer cap element 130. The combination of the proximal edge 147 of the outer cap element 130 forcing the proximal end 173 of the cap snap means 149 in its position and the elevation 157 pushing the deformable region 151 into the cavity 143 of the outer cap element 130 cause proper match of the cap snap feature 149 over the elevation 157, thereby holding the cap 120 in the attached position.

Figure 25:
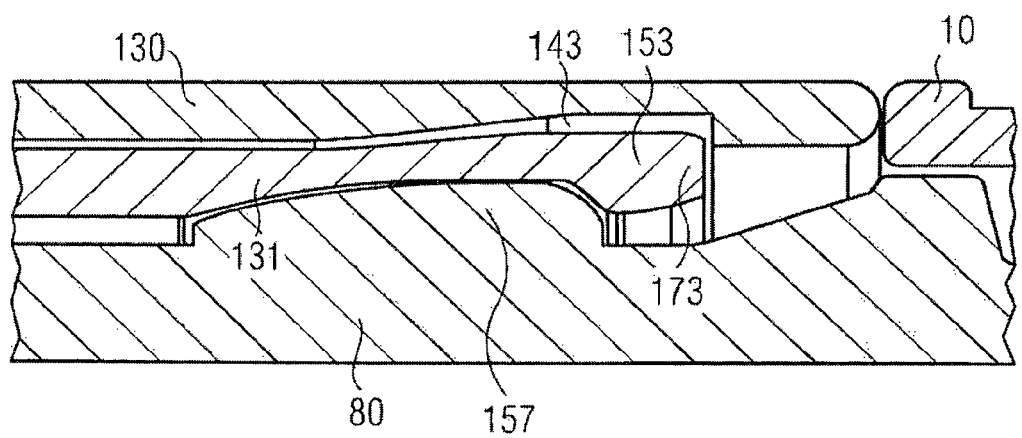
FIG. 25 shows a sectional view of the proximal section of an alternative embodiment of the cap after attachment.

FIG. 25 shows a sectional view of the proximal section of another embodiment of cap 120 after attachment to the drug delivery device 1.

This embodiment differs from the one described above by the design of the inner cap element 131. The proximal end 173 of the cap snap means 149 does not extend over the proximal edge of the cavity 143, which allows a deformation in such a manner that the proximal edge 173 also moves into to the cavity 143 during attachment. In this embodiment less stress impacts to the cap snap means 149 since merely the elevation 157 deforms the snap cap means 149 and the torque is significantly reduced.

The following FIGS. 26 to 30 illustrate the attachment of the clip element 134 which serves as fixing element.

Figure 26:
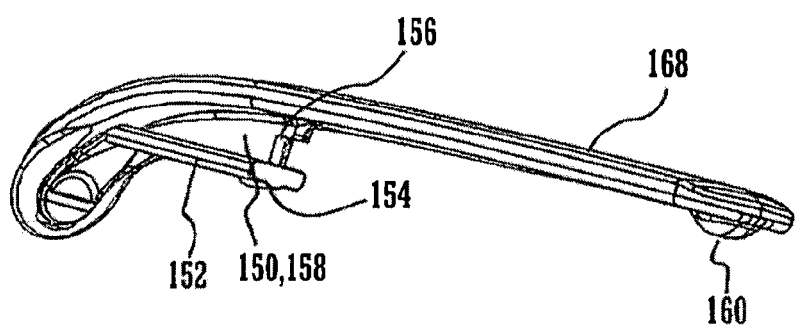
FIG. 26 shows a perspective view of a fixing element.

FIG. 26 shows a fixing element 134 or clip element for a drug delivery device 1, such as a pen-type device. By means of the clip element 134 a fixation or attachment of a cap or cap assembly (see below) of the drug delivery device or the drug delivery device may be fixed to a further component, e.g. a shirt pocket of a user of the device. Accordingly, the fixing element 134 comprises a fixing portion 168 or main body with an elongate shape and a slight curvature at a distal end (left in FIG. 26) of the fixing element 134. The fixing element 134 further comprises a guiding element 150. The guiding element 150 is disposed near the distal end of the fixing element 134 at an inside of the mentioned curvature. The guiding element 150 may constitute or comprise a rail such that the fixing element 150 may be guided by an element receiving the guiding element 150, preferably, along a longitudinal axis of the fixing element or the device. The guiding element extends over less than half of the axial extension of the fixing member 134. The guiding element 150 further comprises a T-shaped cross-section for facilitating the mentioned guiding functionality (cf. also FIG. 29). In order to form the T-shaped section, the guiding element 150, comprises a receiving portion 152. The receiving portion 152 may constitute the horizontal stroke or bar of the "T" of the T-shaped section. Preferably, the receiving portion 152 is configured to be received by one or more openings or apertures of the components to which the fixing element 134 is to be mounted, e.g. in a cap assembly (cf. FIGS. 29 and 30).

Furthermore, the guiding element 150 comprises a guiding portion 158. The guiding portion 158, preferably, constitutes the vertical stroke or bar of the "T" of the T-shaped section of the guiding element 150. The guiding portion 158 may be a web connecting the fixing portion 168 of the fixing element 134 with the receiving portion 152. The guiding portion 158 may further be received by or arranged in one or more openings of the components to which the fixing element 134 is to be mounted, e.g. in the mentioned cap assembly.

The guiding element 150 comprises a connection feature 154 which comprises or constitutes a protrusion protruding radially at an inside of the fixing element 134. Preferably, the connection feature 154 is configured to interact with a corresponding connection feature, e.g. of an inner cap element 131 (cf. FIG. 30). The connection feature 154 is disposed at a proximal end of the guiding element 150. The connection feature 154 may further comprise or constitute a distal face of the guiding element 150.

The guiding element 150 or the fixing element 134 further comprises an abutment feature 156. The abutment feature 156 comprises a radial abutment face with a normal perpendicular to the longitudinal axis of the fixing element 134 and a longitudinal abutment face which is designed to hide or cover over any gaps between the fixing element 134 and the outer cap element 130 resulting from tolerances in manufacture and assembly. The abutment feature 154 is, preferably configured to abut one or more corresponding components to which the fixation element 134 is to be mounted, e.g. in the cap assembly 200 (cf. FIG. 30).

Moreover, the fixing element 134 comprises an attachment feature 160. The attachment feature 160 may be configured to interact with a further component. The attachment feature 160 may comprise or constitute a bump. The attachment feature is, furthermore axially spaced from the guiding element 150 and arranged near a proximal end of the fixing element 134. The attachment feature 160 is, preferably, configured to interact with the outer cap element 130 by means of mechanical contact. Thereby fixation or attachment of a cap assembly or drug delivery device to the further element, such as a shirt pocket of a user of the assembly or the device may be facilitated or aided. Particularly, said mechanical contact may increase friction and therewith the reliability of the attachment of the cap assembly and the further element.

Figure 27:
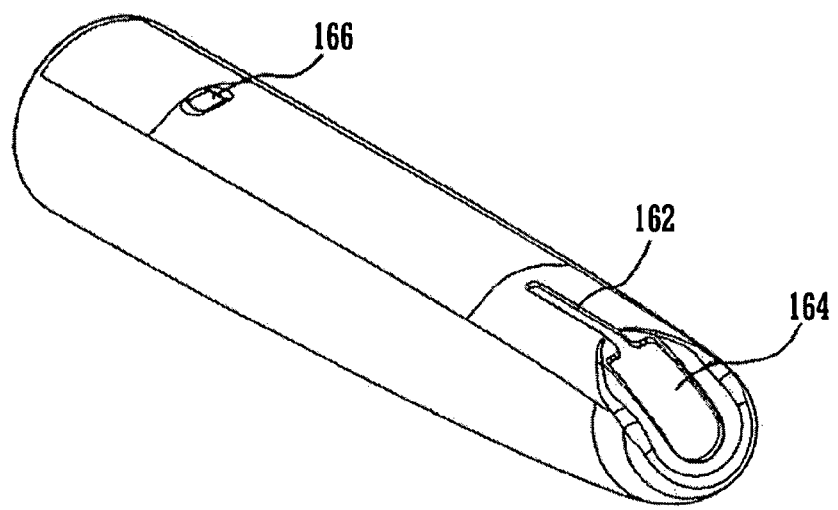
FIG. 27 shows a perspective view of the outer cap element.

FIG. 27 shows a perspective view of an outer cap element 130. The outer cap element 130 comprises an elongate shape. The outer cap element 130 further comprises a sleeve-like shape. Preferably, the outer cap element 130 is made of a metal, e.g. from aluminium. To this effect, the outer cap element 130 is, preferably, formed or fabricated by deep drawing.

The outer cap element 130 further comprises an opening 164. The opening 164 is arranged at a distal end of the outer cap element 130. The opening 164 is, preferably, formed from the outer cap element 130 by punching. The outer cap element may further comprise a proximal opening which is not explicitly indicated in FIG. 27. Formed within the opening 164 is a corresponding guiding feature 162 corresponding to the guiding element 150 described in FIG. 26. The corresponding guiding feature 162 extends—originating from the opening 164—in a proximal direction of the outer cap element 130. The corresponding guiding feature 162 may be a guide slot. The corresponding guiding feature 162 may be configured to receive the guiding portion 158 of the guiding element 150 such that the guiding portion is arranged inside the corresponding guiding feature 162. Preferably, the opening 164, the corresponding guiding feature 162 and the fixing element 134 are configured such that the guiding element 150 can be introduced in or received by the opening 164. When, then, the fixing element is pushed proximally, the guiding portion 158 may be received by or arranged in the corresponding guiding feature 162, wherein the receiving portion 152 is, preferably, only received by the remainder of the opening 164 and arranged inside the outer cap element 130 and/or the inner cap element (cf. FIGS. 29 and 30).

The outer cap element 130 further comprises a depression 166. The depression 166, preferably, receives or interacts with the above-mentioned attachment feature 160 of the fixing element when e.g. the fixing element 134 and the outer cap element 130 are assembled to the cap assembly 200 (cf. FIGS. 29 and 30 below). Preferably, the attachment feature extends into the depression 166 and/or contacts the outer cap element 130 in the depression 166. The depression 166 is axially, particularly proximally, spaced from the opening 164 along a longitudinal axis of the outer cap element 130. The depression 166 is, preferably, shaped according to the attachment feature, i.e. with the same curvature as the mentioned bump of the attachment feature 160 (cf. FIG. 26).

Figure 28:
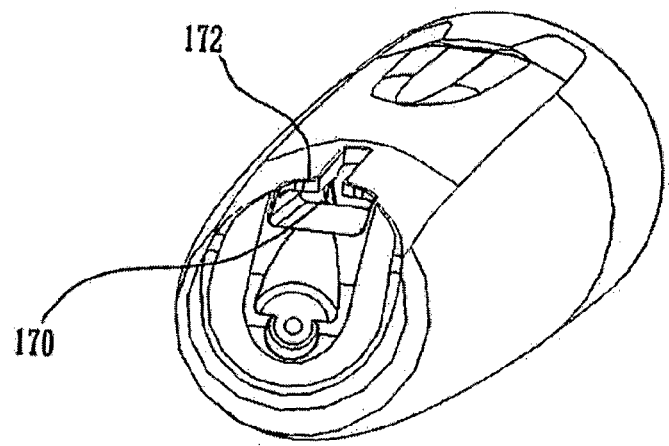
FIG. 28 shows a perspective view of an inner cap element.

FIG. 28 shows a perspective top view of an inner cap element 131. The inner cap element 131 may be a sleeve and configured to be introduced in the outer cap element 130. The inner cap element 131 comprises a corresponding connection feature 170. The corresponding connection feature 170 corresponds to the connection feature 154 of the fixing element 134 such that the fixing element 134 can be connected to the inner cap element 131 by an interaction of the connection feature 154 and the corresponding connection feature 170 (cf. FIGS. 29 and 30). The corresponding connection feature 170 may constitute or comprise a proximal face of the inner cap element 131. The inner cap element 131 further comprises an opening 172. The opening 172 is arranged at or near the distal end of the inner cap element 131. The opening 172 may further be shaped similar to the opening 164 of the outer cap element (cf. FIG. 27).

Figure 29:
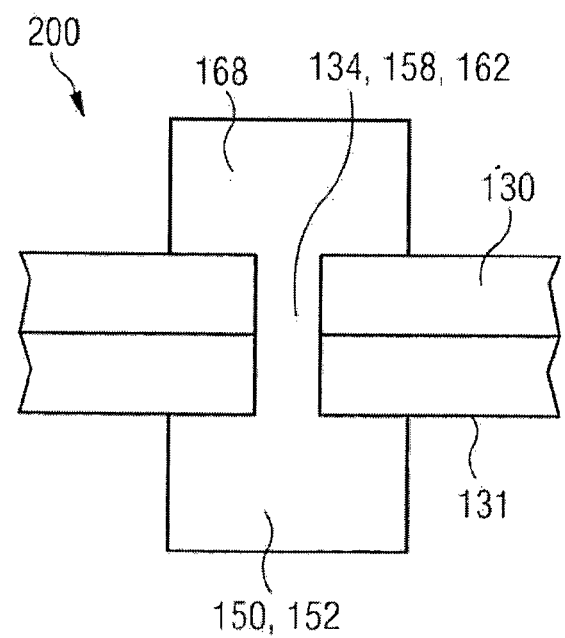
FIG. 29 shows a schematic cross-sectional view of parts of the cap.
Figure 30:
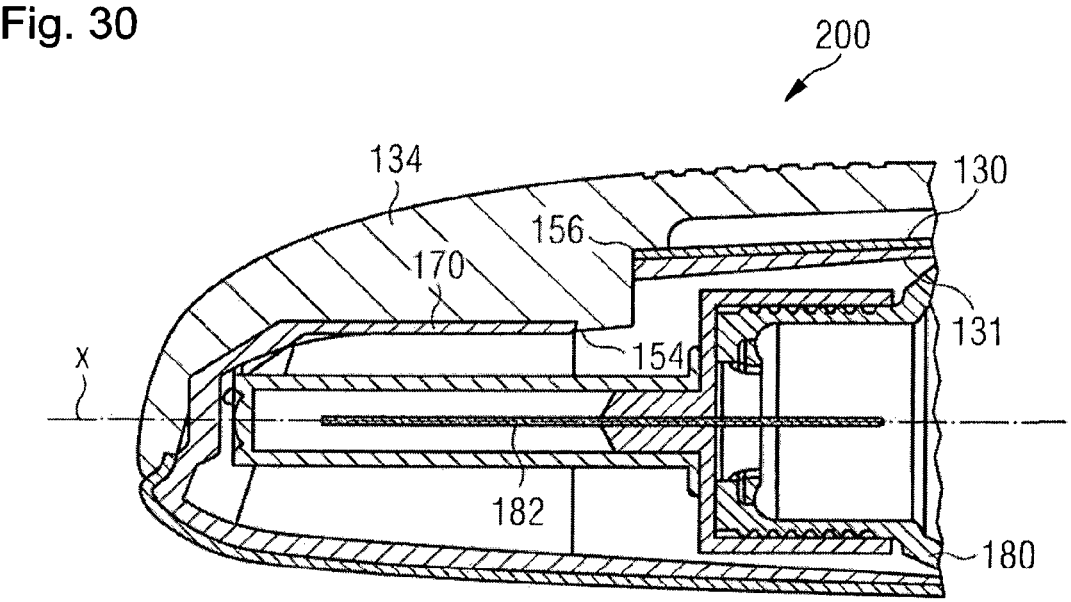
FIG. 30 shows a portion of the cap in a longitudinal section.

FIG. 29 shows a schematic section of parts of a cap assembly 200 (cf. FIG. 30). The assembly 200 comprises the fixing element 134, the outer cap element 130 and the inner cap element 131. FIG. 23 shows the mentioned components in an assembled state. An inner side of the cap assembly 200 is shown at the bottom and an outer part is shown at the top of the section shown in FIG. 29. In the depicted situation, the inner cap element 131 is arranged in the outer cap element 130 and at least a section of the fixing member 134 and/or the guiding element 150 extends through the opening 164 of the outer cap element and, preferably, also through the opening 172 of the inner cap element. To this effect, the openings 164 and 172 may overlap in the cap assembly 200. It is further shown in FIG. 29 that the guiding element 150 comprises the T-shaped section (said T is depicted upside down), as described above. The section of the whole fixing element 134 may, thereby, be shaped H-like. The guiding portion 158 is arranged in the corresponding guiding feature 162 (cf. also FIG. 27). The guiding element 150, particularly the receiving portion 152 may prevent an (outward) radial movement of the fixing element 134 with respect to the outer cap element 130 and/or the inner cap element 131, for example. This is because the corresponding guiding feature 162 is too narrow, as to allow for the receiving portion 152 to radially pass through the corresponding guiding feature 162.

FIG. 30 shows a longitudinal section of parts of the cap assembly 200. The cap assembly comprises a longitudinal axis X. Also, a drug delivery device in which the cap assembly 200 is applied may be shown in FIG. 30.

The fixing element 134 closes the opening 172 of the inner cap element 131 and the opening 164 of the outer cap element 130 such that a rounded shape of the cap assembly 200 results. The connection feature 154 of the fixing element 134 is arranged at least partly in the opening 164 of the outer cap element 130, as well as in the opening 172 of the inner cap element 131 (openings not explicitly indicated in FIG. 30). Particularly, the corresponding guiding feature 162 is configured to receive the receiving portion 152 of the guiding element 150 such that the receiving portion 152 is arranged inside of the outer cap element 130 and also inside the inner cap element 131 (cf. also FIG. 29).

The fixing element 134 and the inner cap element 131 are connected with one another. Particularly, the connection feature 154 interacts with, preferably abuts the corresponding connection feature 17 via a snap interaction such that the fixing element 134 and the inner cap element 131 are connected with respect to one another. The fixing element 134 and the inner cap element 131 are, preferably, reliably connected to one another, as the distal face of the connection feature 154 and the proximal face of the corresponding connection feature 170 abut. In order to connect the mentioned components or during the connection, at least one of the fixing element 134 and the inner cap element 131, may at least slightly be deformed. The connection feature 154 blocks proximal movement (i.e. to the left in FIG. 30) of the inner cap element 131 with respect to the outer cap element 130 such that the inner cap element 131 is retained within the outer cap element 130.

The abutment feature 156 further axially abuts a distal face of the inner cap element 131 and a distal face and a radial face of the outer cap element (faces are not explicitly indicated). By the described abutment, it may be further facilitated that movement of the outer cap element 130 with respect to the inner cap element 131—especially in the distal direction—is blocked and the outer cap element 130 is secured by the fixing element 134. Moreover, the mentioned abutment interaction of the abutment feature 156 provided mechanical stability to the cap assembly 200.

Although this is not explicitly indicated in FIG. 30, the attachment feature 160 of the fixing element 134, preferably, mechanically contacts the depression 166 of the outer cap element 130 (cf. description above).

Also further components e.g. of a drug delivery device, wherein the cap assembly 200 may be applied to, are shown. Such components relate to a cartridge or cartridge holder 180 which may retain a drug (not explicitly indicated). Furthermore, an injection needle 182 is shown which is in fluid communication with the drug from the cartridge or cartridge holder 180. It is shown that the inner cap element 131 accommodates the needle 182 and furthermore at least a section of the cartridge or cartridge holder 180.

The inner cap element may, advantageously, be designed to be mouldable by an injection moulding process with just one core and one cavity insert in the injection mould tooling. Thereby it can be manufactured by a low-cost moulding process.

The cap 120 (cf. FIG. 3) may be or relate to the cap assembly 200. The cartridge or cartridge holder 180 may be or relate to the cartridge 81 and/or to the cartridge holder 80. The clip element may be or relate to the fixing element 134.

The scope of protection is not limited to the examples given herein above. The invention is embodied in each novel characteristic and each combination of characteristics, which particularly includes every combination of any features which are stated in the claims, even if this feature or this combination of features is not explicitly stated in the claims or in the examples. The features of the embodiments mentioned above may be combined. The layout, function, and number of components may be changed in other embodiments.

REFERENCE NUMERALS 1 drug delivery device
10 outer housing part
11 distal part
12 stop
13 aperture
20 inner body
21 external thread
22 splines
23 bayonet features
24 retaining means
25 stop
30 piston rod
31 bearing
32 thread
33 thread
40 driver
41 distal portion
42 proximal portion
43 coupler
44 thread
45 stop faces
46 splines
47 teeth features
48 fingers
49 bearing surface
50 dose nut
51 stop faces
52 external ribs
53 internal thread
60 display member
61 number sleeve
62 dial sleeve
63 stop face
64 thread
65 teeth
66 contact features
67 opposite faces
68 clicker
7 button
71 clicker
72 end face
73 fingers
74 snap features
80 cartridge holder
81 cartridge
82 bayonet connection
83 aperture
84 distal end
90 clutch
91 drive sleeve splines
92 clutch biasing teeth
93 snap features
94 splines
95 clutch teeth
100 clicker
101 distal clicker part
102 proximal clicker part
103 spring
104 splines
105, 106 clicker teeth
107 external splines
108 shaped splines
109 clutch biasing teeth
110 spring
120 cap
121 distal end
122 proximal end
230 window
130 outer cap element
131 inner cap element
134 clip element
135 aperture of cap
136 aperture of outer housing part
137 end face (of cap)

141 proximal section
143 cavity
147 edge
149 cap snap means
151 deformable region
153 nose
155 cap retention feature
157 elevation
161 folded end
171 cavity
173 proximal end
150 guiding element
152 receiving portion
154 connection feature
156 abutment feature
158 guiding portion
160 attachment feature
162 corresponding guiding feature
164 opening (outer cap element)
168 fixing portion
166 depression
170 corresponding connection feature
172 opening (inner cap element)
180 cartridge/cartridge holder
182 injection needle
200 cap assembly
X longitudinal axis

The invention claimed is:

1. A drug delivery device comprising:
a cartridge holder comprising a threaded distal end to which a needle assembly is attachable and a cap retention feature comprising an elevation proximal to the threaded distal end, the cartridge holder configured to receive a cartridge containing a medicament to be dispensed; and
a cap having a distal end, a proximal end, and an opening at the proximal end, the cap comprising:
an outer cap element, and
an inner cap element being located inside the outer cap element, the inner cap element comprising a deformable region and a cap snap feature, the cap snap feature being located on the inside of a proximal section of the inner cap element and configured for engaging with the cap retention feature located on the cartridge holder,
wherein the deformable region of the inner cap element is deformable into a gap between the inner cap element and the outer cap element,
wherein the gap is formed as a cavity comprised by the outer cap element,
wherein the cap retention feature is suitable for forming a snap connection with the cap snap feature,
wherein a proximal slope of a nose of the cap snap feature with respect to a longitudinal axis of the drug delivery device is less steep than a distal slope of the nose of the cap snap feature with respect to the longitudinal axis,
wherein the proximal slope of the nose is at a proximal end of the nose and the distal slope of the nose is at a distal end of the nose, and
wherein the outer cap element has a folded proximal end comprising a folded back proximal lip, the folded back proximal lip forming a proximal edge of the cavity of the outer cap element.

2. The drug delivery device according to claim 1, wherein the drug delivery device comprises a cartridge containing a pharmaceutically active compound.

3. The drug delivery device according to claim 1, wherein the cap retention feature is arranged in a proximal section of the cartridge holder.

4. The drug delivery device according to claim 1, wherein the outer cap element is made of metal.

5. The drug delivery device according to claim 1, wherein a proximal section of the outer cap element is deep drawn.

6. The drug delivery device according to claim 1, wherein a thickness of the outer cap element in a region of the cavity is smaller than a thickness of the outer cap element in a region distal to the cavity.

7. The drug delivery device according to claim 1, wherein the cap snap feature is located in the deformable region or adjacent to the deformable region.

8. The drug delivery device according to claim 1, wherein a proximal end of the cap snap feature is located proximally with respect to a proximal edge of the cavity of the outer cap element or the proximal end of the cap snap feature is located distally with respect to the proximal edge of the cavity of the outer cap element.

9. The drug delivery device according to claim 1, wherein the cap snap feature comprises a raised portion.

10. The drug delivery device according to claim 1, wherein a thickness of the inner cap element in at least a part of the deformable region is smaller than a thickness of the inner cap element in a region distal to the deformable region.

11. The drug delivery device according to claim 1, wherein the cap snap feature comprises a snap cavity configured to engage the cap retention feature of the cartridge holder of the drug delivery device.

12. The drug delivery device according to claim 1, wherein the inner cap element is made of plastic.

13. The drug delivery device according to claim 1, wherein the inner cap element and the outer cap element are sleeve-shaped.

14. The drug delivery device according to claim 1, further comprising a fixing element with a connection feature,
wherein the outer cap element has an opening, and the inner cap element comprises a corresponding connection feature, and
wherein a section of the fixing element extends through the opening of the outer cap element such that the fixing element is connected to the inner cap element by an interaction of the connection feature and the corresponding connection feature.

15. A cap for a drug delivery device, the cap having a distal end, a proximal end, and an opening at the proximal end, the cap comprising:
an outer cap element; and
an inner cap element located inside the outer cap element, the inner cap element comprising a deformable region and a cap snap feature, the cap snap feature being located on the inside of a proximal section of the inner cap element and configured for engaging with a cap retention feature located on a cartridge holder of the drug delivery device,
wherein:
the deformable region of the inner cap element is deformable into a continuous gap between the inner cap element and the outer cap element, a proximal edge of the continuous gap being defined by a folded proximal end of the outer cap element, and a distal edge of the continuous gap being adjacent to the deformable region of the inner cap element,
a proximal slope of a nose of the cap snap feature with respect to a longitudinal axis of the drug delivery device is less steep than a distal slope of the nose of the cap snap feature with respect to the longitudinal axis, and the proximal slope of the nose is at a proximal end of the nose and the distal slope of the nose is at a distal end of the nose.

16. A drug delivery device comprising:

a cartridge holder; and a cap removably positioned over the cartridge holder, the cap having a distal end, a proximal end, and an opening at the proximal end, the cap comprising:

an outer cap element;

an inner cap element located inside the outer cap element, the inner cap element comprising a deformable region and a cap snap feature, the cap snap feature being located on the inside of a proximal section of the inner cap element and configured for engaging with a cap retention feature located on the cartridge holder of the drug delivery device, the deformable region comprising a reduced thickness region located distal to the cap snap feature, wherein the reduced thickness region comprises a reduced thickness relative to a portion distal to and a portion proximal to the reduced thickness region, wherein the deformable region of the inner cap element is deformable into a gap between the inner cap element and the outer cap element when the cap is removed from the cartridge holder, wherein the gap is formed as a cavity defined by the outer cap element, and wherein a proximal slope of a nose of the cap snap feature with respect to a longitudinal axis of the drug delivery device is less steep than a distal slope of the nose of the cap snap feature with respect to the longitudinal axis, wherein the proximal slope of the nose is at a proximal end of the nose and the distal slope of the nose is at a distal end of the nose, and wherein the outer cap element has a folded proximal end comprising a folded back proximal lip, the folded back proximal lip forming a proximal edge of the cavity of the outer cap element.

* * * * *

UNITED STATES PATENT AND TRADEMARK OFFICE
CERTIFICATE OF CORRECTION

PATENT NO. : 11,052,200 B2  
APPLICATION NO. : 14/914476  
DATED : July 6, 2021  
INVENTOR(S) : David Aubrey Plumptre Page 1 of 1

It is certified that error appears in the above-identified patent and that said Letters Patent is hereby corrected as shown below:

In the Claims

In Column 25, Line 12, Claim 16, after "element;" insert -- and --

Signed and Sealed this  
Twenty-first Day of December, 2021

Drew Hirshfeld  
*Performing the Functions and Duties of the*  
*Under Secretary of Commerce for Intellectual Property and*  
*Director of the United States Patent and Trademark Office*